US009629955B2

(12) United States Patent
Bresina et al.

(10) Patent No.: US 9,629,955 B2
(45) Date of Patent: Apr. 25, 2017

(54) DRUG OR FLUID DELIVERY DEVICES

(71) Applicant: Smiths Medical ASD, Inc., Rockland, MA (US)

(72) Inventors: Timothy Bresina, Shoreview, MN (US); Renee Robert, Shoreview, MN (US); Chad Amborn, Minneapolis, MN (US)

(73) Assignee: SMITHS MEDICAL ASD, INC., Rockland, MA (US)

( * ) Notice: Subject to any disclaimer, the term of this patent is extended or adjusted under 35 U.S.C. 154(b) by 90 days.

(21) Appl. No.: 14/432,375

(22) PCT Filed: Oct. 7, 2013

(86) PCT No.: PCT/US2013/063664
§ 371 (c)(1),
(2) Date: Mar. 30, 2015

(87) PCT Pub. No.: WO2014/058770
PCT Pub. Date: Apr. 17, 2014

(65) Prior Publication Data
US 2015/0250940 A1    Sep. 10, 2015

Related U.S. Application Data

(60) Provisional application No. 61/713,199, filed on Oct. 12, 2012.

(51) Int. Cl.
*A61M 5/142* (2006.01)
*A61J 1/10* (2006.01)
*A61J 1/14* (2006.01)

(52) U.S. Cl.
CPC ............... *A61M 5/142* (2013.01); *A61J 1/10* (2013.01); *A61J 1/1493* (2013.01);
(Continued)

(58) Field of Classification Search
CPC ............ A61M 2205/123; A61M 5/142; A61M 5/14228; A61M 5/14232; A61J 1/10; A61J 1/1493
See application file for complete search history.

(56) References Cited

U.S. PATENT DOCUMENTS 3,661,143 A    5/1972 Henkin
4,381,846 A    5/1983 Heck
(Continued)

FOREIGN PATENT DOCUMENTS

EP    0278670        8/1988
FR    2871062 A1    12/2005
(Continued)

OTHER PUBLICATIONS

International Preliminary Report on Patentability and Written Opinion of the International Searching Authority, report issued Apr. 14, 2015, 8 pages.
(Continued)

*Primary Examiner* — Quynh-Nhu H Vu
(74) *Attorney, Agent, or Firm* — Patterson Thuente Pedersen, P.A.

(57) ABSTRACT

A drug or fluid delivery device includes a pump having a control module. A cassette is removably mounted to the control module. A reservoir is contained within the cassette, and contains a fluid to be delivered to a patient. A protrusion extends from an interior surface of the cassette, creating and maintaining a crease in the reservoir as the fluid is emptied therefrom, thereby creating a fluid path along which the fluid travels to reduce occurrences of the reservoir deleteriously sealing off pockets of fluid as the reservoir is emptied.

1 Claim, 11 Drawing Sheets

(52) U.S. Cl.
CPC ..... *A61M 5/14228* (2013.01); *A61M 5/14232* (2013.01); *A61M 2205/123* (2013.01)

(56) References Cited

U.S. PATENT DOCUMENTS

| | | | |
|---|---|---|---|
| 4,559,038 A | | 12/1985 | Berg |
| 4,601,410 A | | 7/1986 | Bond |
| 4,772,278 A | | 9/1988 | Baber |
| 4,959,062 A | | 9/1990 | Gellman |
| 4,998,990 A | * | 3/1991 | Richter .................. B31B 19/90 222/105 |
| 5,092,856 A | | 3/1992 | Johnston |
| 5,368,562 A | * | 11/1994 | Blomquist ............ A61M 5/172 604/246 |
| 5,647,511 A | | 7/1997 | Bond |
| 5,743,435 A | * | 4/1998 | Tomic .................. B65D 77/065 222/105 |
| 5,743,878 A | | 4/1998 | Ross |
| 6,027,438 A | | 2/2000 | Frazier |
| 6,102,252 A | * | 8/2000 | Overman ........... B65D 75/5877 222/105 |
| 6,123,686 A | | 9/2000 | Olsen |
| 6,279,780 B1 | | 8/2001 | Rousselet |
| 6,607,097 B2 | | 8/2003 | Savage |
| 6,609,636 B1 | | 8/2003 | Petriekis |
| 6,715,644 B2 | | 4/2004 | Wilford |
| 6,851,579 B2 | * | 2/2005 | Savage ............. B65D 75/5877 220/62.12 |
| 7,044,940 B1 | | 5/2006 | Hahn |
| 7,357,276 B2 | | 4/2008 | Savage |
| 7,445,131 B2 | | 11/2008 | Pottish |
| 7,470,253 B2 | | 12/2008 | Kriesel |
| 7,686,187 B2 | | 3/2010 | Pottish |
| 7,972,321 B2 | | 7/2011 | Fangrow |
| 7,993,304 B2 | | 8/2011 | Kriesel |
| 8,021,334 B2 | | 9/2011 | Shekalim |
| 2002/0148857 A1 | | 10/2002 | Savage |
| 2010/0121306 A1 | | 5/2010 | Yodfat |
| 2010/0228196 A1 | | 9/2010 | Wyss |
| 2011/0133946 A1 | * | 6/2011 | Kopp .................. A61M 5/142 340/679 |
| 2012/0136304 A1 | | 5/2012 | Wyss |

FOREIGN PATENT DOCUMENTS

| | | |
|---|---|---|
| GB | 732761 | 6/1955 |
| WO | WO8402648 | 7/1984 |
| WO | WO 98/13080 A2 | 4/1998 |
| WO | WO 2006/024650 A2 | 3/2006 |
| WO | WO 2010105718 A | 9/2010 |
| WO | WO 2011018753 A | 2/2011 |

OTHER PUBLICATIONS

European Search Report, Application No. 13844809.7, dated Mar. 21, 2016, 7 pages.

International Application No. PCT/US2013/063664, filed Oct. 7, 2013, International Search Report, mailed Jan. 2, 2014, 4 pages.

* cited by examiner

DRUG OR FLUID DELIVERY DEVICES

RELATED APPLICATION

This application is a National Phase entry of PCT Application No. PCT/US2013/063664 filed Oct. 7, 2013, which application claims the benefit of priority to U.S. Provisional Patent Application No. 61/713,199 filed Oct. 12, 2012, the entire disclosures of which are incorporated herein by reference.

TECHNICAL FIELD

This disclosure relates generally to medical devices, and more specifically to drug or fluid delivery devices including cassette and reservoir assemblies.

BACKGROUND

Drug or fluid delivery devices such as drug pumps are known. Drug pumps often are grouped into types such as so-called ambulatory pumps, peristaltic pumps, syringe pumps, gravity-feed pumps, elastomeric pumps, and multi-channel pumps. Although these groupings are often helpful for a general understanding and characterization of drug pumps per se, such terminology is neither limiting nor conclusive and may at times be used interchangeably and variably in the medical arts.

Ambulatory infusion pumps are portable drug or fluid delivery devices that are used to deliver drugs or fluids typically including, but not limited to: therapeutic agents; nutrients; drugs; medicaments such as antibiotics, blood clotting agents, and analgesics; and other fluids to a patient, typically for purposes of treating physiological and other medical conditions. The devices can be used to introduce the drugs or fluids into patients' bodies utilizing any of several routes such as intravenously, subcutaneously, arterially, or epidurally. Such devices may also provide a so-called PCA (or, "patient controlled analgesia") function, depending upon a particular medical need.

Ambulatory infusion pump assemblies generally include: a control module with a pumping mechanism and an interface for programming of the pump by a healthcare practitioner or patient; a cassette releasably connected to the control module; a reservoir, bag, or other container with the cassette which contains the fluid to be delivered; and an infusion set or fluid line containing an assembly of tubing, luers, connectors, valves, cannulae, or the like for delivering the fluid from the cassette to the patient. A patient receives a dose of medication or other fluid by activation of a control on, or connection to, the control module such as a push-button activator or switch, or in some embodiments via a remote dose cord or an automatic, computerized program. Such activation starts the pumping mechanism in the pump which delivers a measured dose of the fluid from the reservoir, bag, or other container (collectively herein, "reservoir") in the cassette to the patient via the fluid line within an allowable time interval as programmed.

When a reservoir is emptied, the cassette is released from the pump and the depleted reservoir is removed from the cassette for disposal—or the entire cassette is disposed. A new or refilled reservoir is placed into the cassette, or a new cassette is obtained; and the cassette is then remounted to the control module. When the fluid line has been primed, the pump can then be restarted to continue infusion or delivery of the fluid to the patient.

The cassette reservoir typically comprises a bag formed from a flexible polymer material that is sealed at its edges, in contrast to a relatively rigid material such as glass or hard plastic, for ease of manufacture and handling. However, it has been found that pumping a flexible reservoir to a completely empty state can be challenging. This may happen particularly when using a vacuum to draw a viscous fluid from the reservoir, because the typically flexible reservoir can collapse as it empties, sealing off pockets of fluid that are thus largely inaccessible for delivery to the patient. This can result in a false or premature signal of an empty reservoir, or inconsistent metering and delivery of the remaining fluid to the patient. This is especially a concern when the fluid being delivered is of high value such that it is desired to minimize or eliminate any waste, or if consistent metering and delivery of the fluid to the patient is highly critical in order to avoid over- or under-dosing.

Known systems and methods for addressing these issues may be highly complex—which may likely make such a pump more costly—or may be difficult or impossible to remedy, thereby likely requiring replacement of at least a part of the pump assembly. Therefore, it would be particularly useful and advantageous to provide a fluid delivery device including a cassette and reservoir assembly that is capable of satisfactory emptying of the reservoir.

SUMMARY

This disclosure describes novel and inventive drug or fluid delivery devices. This disclosure also describes novel and inventive features and uses of fluid delivery devices.

In aspects of subject matter hereof, a fluid delivery device includes a pump having a control module that is removably mounted to a cassette and reservoir assembly. The cassette and reservoir assembly comprises a flexible reservoir enclosed within a cassette and containing a fluid for delivery to a patient. A fluid line, such as an infusion set or a series of tubing, connectors, valves, and cannulae, creates selective fluid communication from the reservoir to a patient via selective pumping action by the pump. Upon activation of the pump, a volume of fluid is expelled from the reservoir and pumped through the fluid line to the patient. This process may proceed, intermittently or continuously, until the reservoir is satisfactorily emptied. The reservoir and cassette assembly further includes means for facilitating relatively consistent fluid flow from the reservoir, while ensuring substantially complete emptying of the reservoir such that no significant volume of fluid is wasted. As used throughout this document, the phrases "satisfactory emptying", "satisfactorily emptied", and the like, are intended to refer to desirable characteristics of reservoir emptying depending upon a particular embodiment and desired uses of such devices such as, for example: complete emptying; nearly complete emptying; and relatively consistent emptying to desired volumes within desired ranges.

In one aspect of subject matter hereof, the means for facilitating the fluid flow from the reservoir comprises a protrusion extending from an interior surface or housing of the cassette. The protrusion creates and maintains a desired fold or crease in the reservoir as it empties, thereby creating a defined channel or fluid path along which the fluid travels to reduce occurrences of the reservoir deleteriously sealing off pockets of fluid as aforementioned.

In another aspect of subject matter hereof, one or more defined fluid paths are preformed within the reservoir. In one example, at least one seal is provided within the reservoir. In another example, a material flap is provided within the reservoir. The material flap is either a separate piece of material sealed, adhered, or otherwise secured to the wall of the reservoir, or it is excess material formed as a pleat, tuck, or other intentional appendage along the reservoir wall. In another example, an interior surface of the reservoir is textured, e.g. by raised discrete portions, thereby forming a series or network of channels. Each of these examples provides for a defined fluid path thereby facilitating flow through and out of the reservoir.

In other aspects of subject matter hereof, a tube extends within the reservoir to create a fluid path. The tube facilitates a relatively consistent flow path along and within the tube. Perforations can be formed in the tube to further enable flow through and along the tube.

In yet other aspects of subject matter hereof, the outlet or filling port of the reservoir is located at positions other than, conventionally, a top corner of the reservoir. Thus, location of the outlet or filling port toward, e.g., a bottom of the reservoir could further aide in satisfactory emptying of the reservoir.

In further aspects of subject matter hereof the outlet or filling port of the reservoir is, as aforementioned, located at positions other than a top corner of the reservoir. Such locations of the outlet or filling port could promote creation of a fold or folds in the reservoir to provide a fluid path or paths, to thereby facilitate flow through the reservoir and satisfactory emptying thereof.

In still further aspects of subject matter hereof, an additional, second port could be provided in the reservoir. The presence of a second port would tend to promote channeling and flow of fluid from the reservoir. Provision of a second port could also enable an easier reservoir filling process, and more complete filling by aiding in air removal from the reservoir through the outlet port as the reservoir is filled via the second port.

BRIEF DESCRIPTION OF THE DRAWINGS

Subject matter hereof is illustrated by way of example and not limitation in the figures of the accompanying drawings in which.

While the subject matter hereof is amenable to various modifications and alternative forms, specifics thereof have been shown by way of example in the drawings and will be described in detail. It should be understood, however, that the intention is not to limit the subject matter hereof to the particular embodiments described. On the contrary, the intention is to cover all modifications, equivalents, and alternatives falling within the spirit and scope of the subject matter hereof.

DETAILED DESCRIPTION

Figure 1:
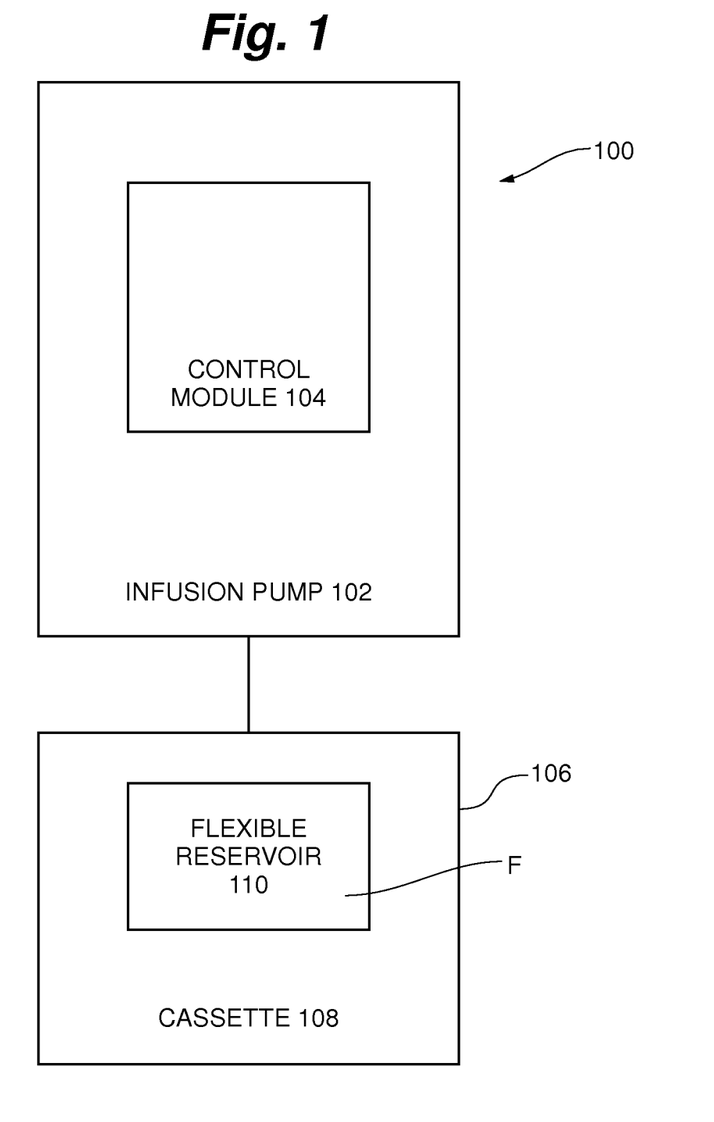
FIG. 1 is a block diagram of a fluid delivery device.

As illustrated generally in FIG. 1, a fluid delivery device 100 generally comprises an ambulatory infusion pump 102 including a control module 104 and a removable cassette and reservoir assembly 106 that is selectively and removably mounted on module 104. Cassette and reservoir assembly 106 includes a cassette 108 and a flexible reservoir 110 housed within cassette 108, reservoir 110 containing a fluid F to be delivered to a patient via pump 102. Cassette and reservoir assembly 106 is configured to provide satisfactory emptying of reservoir 110, as described in more detail in the example embodiments infra.

Although described by example or otherwise contemplated herein in a general context of infusion pumps comprising a control module and a removable cassette, it is to be appreciated and understood that subject matter hereof may be advantageously provided with virtually any device for drug or fluid delivery which utilizes some type of fluid reservoir or container such as also, for example, an intravenous solution drip bag (an "IV drip")—irrespective of a control module or a cassette, and also irrespective of whether a particular embodiment utilizes an enclosed fluid reservoir or a remote fluid reservoir.

In an embodiment of subject matter hereof, means for satisfactory emptying of the reservoir are incorporated into a configuration of at least one of the cassette and the reservoir. As such, satisfactory emptying of the reservoir could possibly reduce or even eliminate an occurrence of false alarms that the reservoir is empty, and provide for relatively consistent fluid delivery to a patient via the fluid line through the pump. This is particularly advantageous when small fluctuations or variations in dosage can have significant effects on the patient receiving the fluid. Furthermore, the means could possibly provide for virtually complete emptying of the reservoir such that no significant volume of fluid is unused. This could be particularly advantageous when the fluid is a relatively expensive medicament, drug, nutrient, or other therapeutic fluid.

Regardless of a particular embodiment, it is to be appreciated and understood that reference is herein made to a "pump" and a "control module" separately, to facilitate understanding of drug or fluid delivery devices as disclosed by example or otherwise contemplated herein generally. Thus, a control module could be software within a drug pump; and a drug pump and a control module could be combined physically in one device or be separate components. Typically, an ambulatory drug pump includes a control module with an interconnectable, removable cassette. The cassette may be linked to an enclosed fluid reservoir disposed within the cassette or a remote fluid reservoir external to the cassette, as aforementioned. The control module may include a pump mechanism for pumping fluid from the fluid reservoir to a patient. The control module may also include a control system having a pump application program for providing a desired particular therapy to a patient such as, e.g., antibiotic therapy, chemotherapy, pain control therapy, and nutritional therapy. The control module may also include means for providing and enabling patient-specific settings which are accessible by the pump application program to deliver the particular fluidic therapy to the patient. The control system may include a display and a keyboard. A communication port may be provided in the control module to transfer information to and from the control system.

Figure 2:
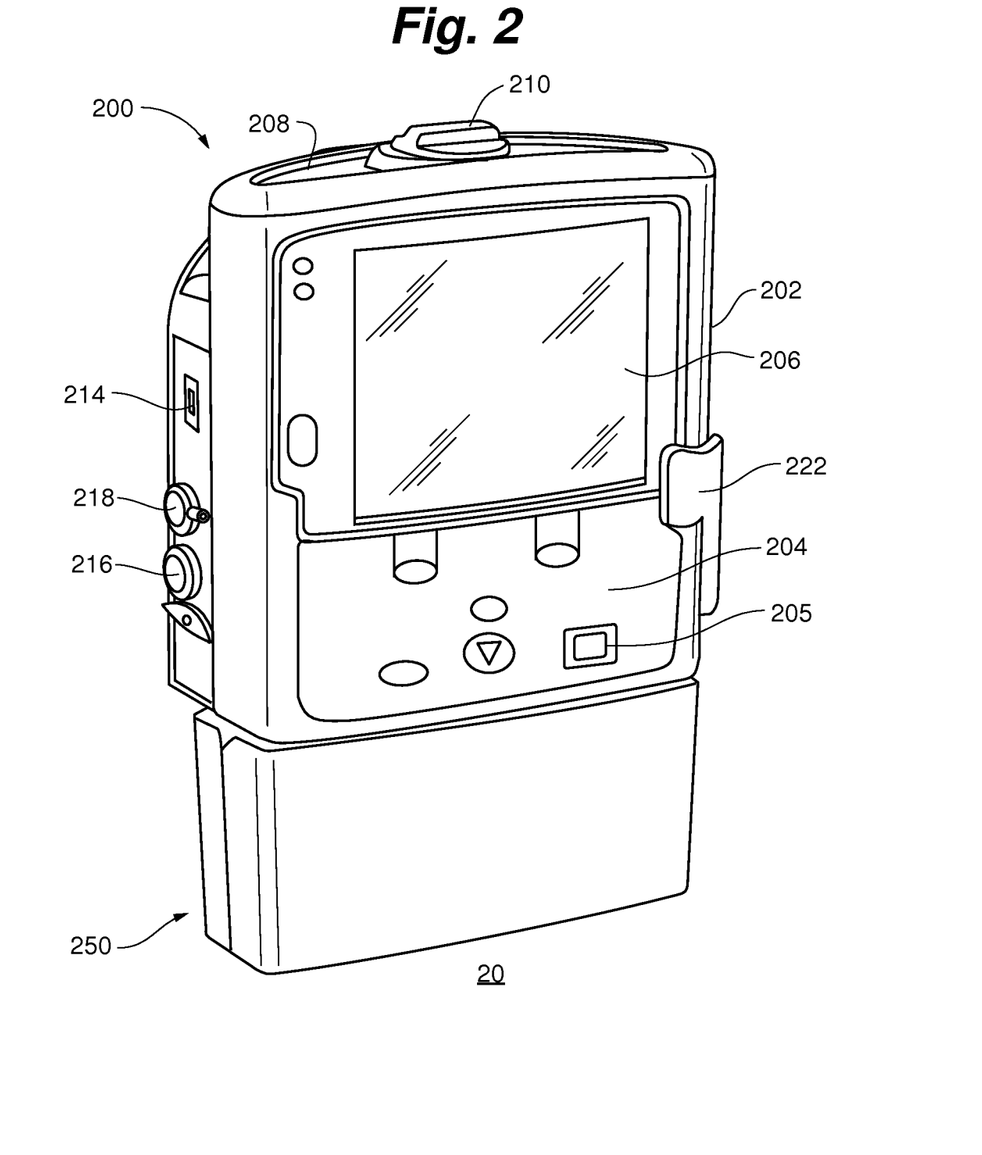
FIG. 2 is a front perspective illustration of one embodiment of a fluid delivery device.
Figure 2A:
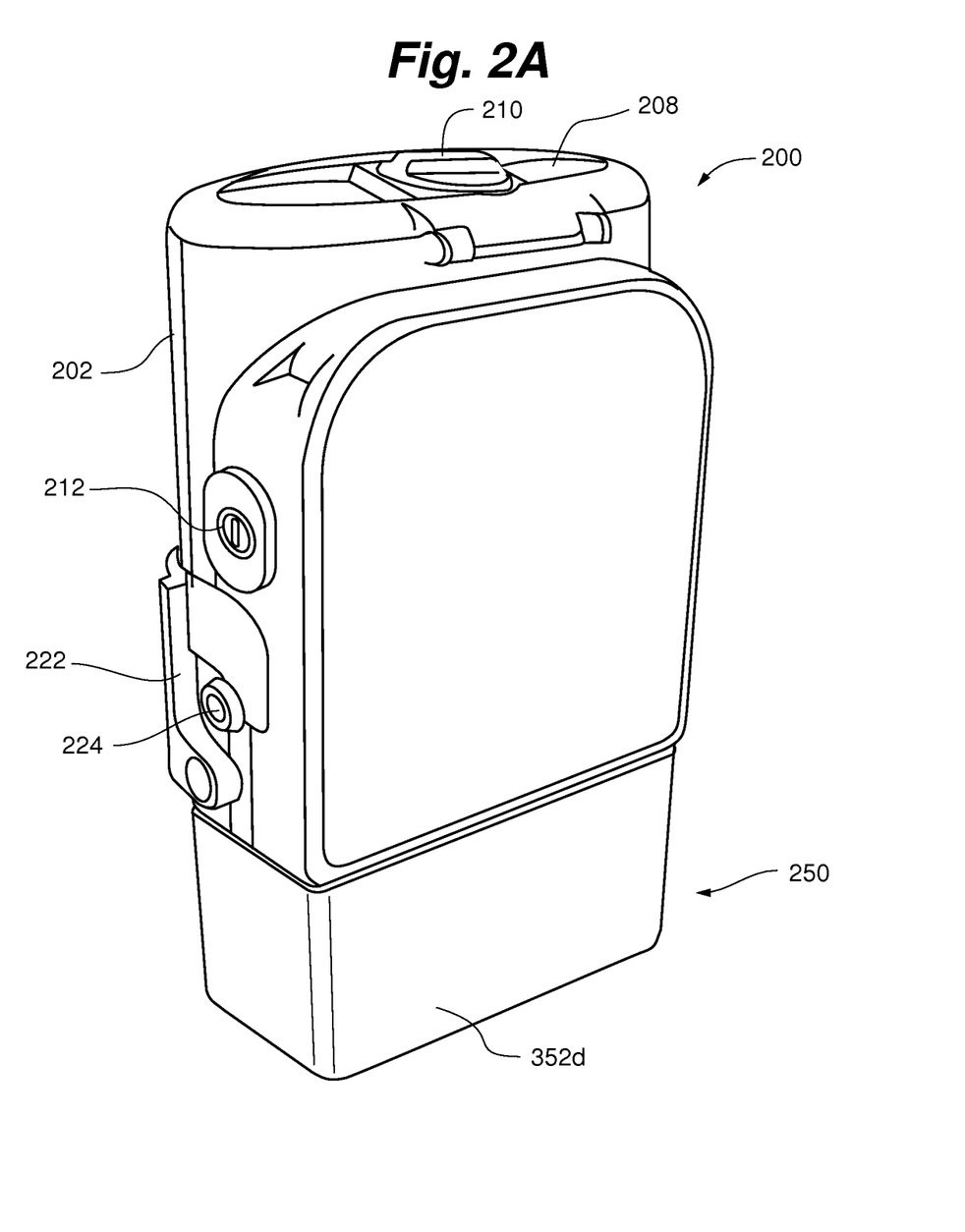
FIG. 2A is a back perspective illustration of the embodiment of the fluid delivery device shown in FIG. 2.

With particular reference now to FIGS. 2 and 2A, an example of a fluid delivery device 20 includes an ambulatory infusion pump 200 having a control module 202 which is selectively mounted to a removable cassette and reservoir assembly 250. A latch 222 on control module 202 is rotatably operable to secure cassette and reservoir assembly 250 to module 202. A lock 224 is operable to prevent or inhibit latch 222 from being unsecured, such as by an unauthorized person. Control module 202 includes a keyboard 204 with a plurality of keys 205 for user inputs to module 202. Control module 202 further includes a display 206, such as a graphical user interface, for displaying information concerning operation of module 202, and thus pump 200—and, in general, device 20. A communication port 214 allows for electronic communication between pump 200 and an external device located either locally or remotely relative to pump 200. An external power supply port 216 allows for connection of an external power supply to operate pump 200 if use of an onboard battery (in battery compartment 208, accessible via battery door access knob 210) is not desired. A remote dosing command port 218 allows for operation of pump 200 by way of a so-called "remote dose cord."

Figure 3:
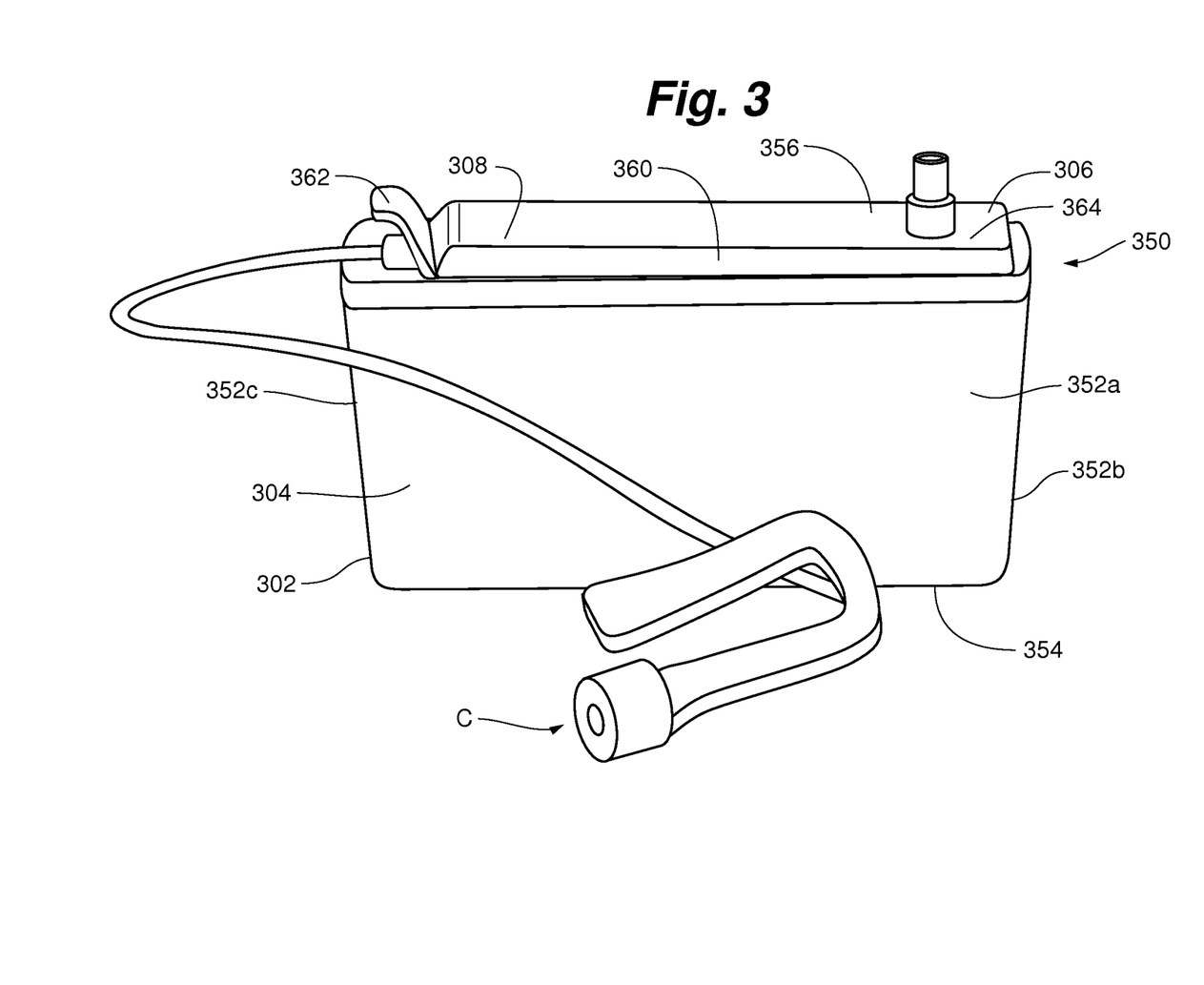
FIG. 3 is a front perspective illustration of a cassette and reservoir assembly.

Referring to FIG. 3, cassette and reservoir assembly 350 includes removable cassette 302 and reservoir 304 enclosed within cassette 302. Cassette 302 generally comprises a relatively rigid container having four sidewalls 352a, 352b, 352c, and 352d (shown in FIG. 2A), a bottom wall 354, and a top plate 356 defining an interior volume. It is to be appreciated and understood that cassette 302 could have more or less than four sidewalls defining a container of any of a variety of shapes, as well as a construction that could be characterized as being less than relatively rigid. In one non-limiting embodiment, plate 356 is removable to allow access to an interior of cassette 302. In another non-limiting embodiment, at least one sidewall 352 is selectively removable from the other sidewalls thereby allowing access to the interior of cassette 302. An exterior surface 360 of plate 356 includes structure, e.g. hooks, ribs, and/or protrusions 362 for removable engagement with control module 202 as described above.

Cassette 302 can be formed or molded from a plastic or polymeric material including, but not limited to, polycarbonate, ABS, polypropylene, polyvinyl chloride, or any other material or blend of materials which provide desirable properties in construction and use of a cassette in embodiments. Cassette 302 also can comprise some other material in embodiments, such as metal, glass, an alloy, rubber, composites, and combinations of any of these or other materials, also can be used in embodiments. Cassette 302 can be transparent, opaque, translucent, or tinted or otherwise colored. In one particular embodiment, cassette 302 comprises a translucent, pigmented rigid plastic container, the pigment corresponding to a specific therapeutic fluid or medicament or a fluid for a specific therapy. The translucent nature allows viewing of the interior volume.

Reservoir 304 generally can comprise, in embodiments, a flexible bag that is formed from a polymeric film material including, but not limited to, polyethylene, polypropylene, polyvinyl chloride, EVA, or any other material or blend of materials which provide desirable properties in construction and use of a reservoir. Reservoir 304 includes at least one outlet or filling port 306, and a tube 308 extending outwardly from port 306. Tube 308 extends from the interior of cassette 302 through aperture 364 of plate 356. It is to be appreciated that tube 308 could actually comprise two tube materials of different diameters to optimize functioning of an infusion pump, with the two tube materials being joined together by any suitable fluid-tight means. Thus, for example, in an embodiment such as shown in FIG. 3, a portion of tube 308 that extends across plate 356 is of a diameter that is larger than another portion of tube 308 that extends outwardly from cassette 302 (initially to the left in the drawing). Tube 308 can further comprise connectors (reference "C" in the drawing) such as male or female luers, and other connectors, filters, and clamps, for operably connecting to a fluid line such that the reservoir is in selective fluid communication with a patient via control module 202 of FIG. 2.

Reservoir 304 is sized such that when it is filled with a fluid, it fits within the interior of cassette 302. As the fluid is expelled from reservoir 304 via a pumping mechanism of control module 202, reservoir 304 collapses upon itself, thereby decreasing its volume as fluid is expelled. Although infrequently, coincidentally in some cases as reservoir 304 so empties and collapses, a fold or crease may advantageously form and extend at least a portion of a distance between top and bottom portions of the reservoir, thereby creating a channel which would significantly reduce a likelihood that a portion of the reservoir deleteriously seals off fluid as aforementioned, as the fluid moves along such fold or crease.

Figure 4:
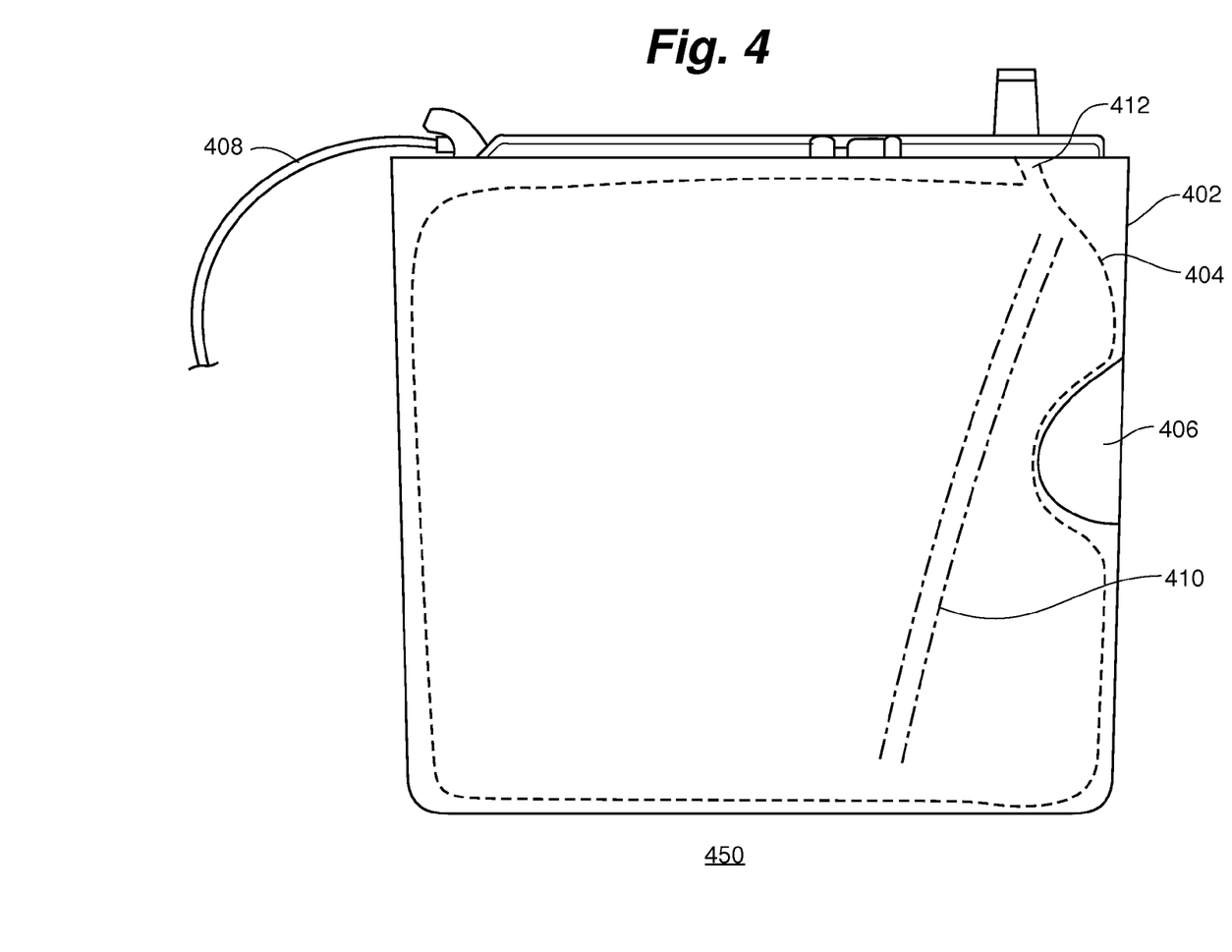
FIG. 4 is a front illustration of an embodiment of a cassette and reservoir assembly according to subject matter hereof.

Thus, in an example embodiment, and referring now to FIG. 4, cassette and reservoir assembly 450 includes a cassette 402 and a reservoir 404 enclosed within cassette 402. At least one protrusion 406, such as a bump or rib, extends from one of the sidewalls, and into the interior volume of cassette 402, such that it is in contact with a portion of reservoir 404. Protrusion 406 is configured to create and maintain a crease or fold 410 along a surface of reservoir 404 as it empties, thereby creating a defined path or channel for a fluid within reservoir 404 to eventually flow to outlet port 412 and then outwardly to tube 408 in use and operation of assembly 450.

It is to be appreciated and understood that in a particular embodiment, the protrusion could have virtually any shape, profile, or geometry. The protrusion could, for example, be rounded, pointed, shallowly or sharply peaked or edged, elongated, or ribbed, etc., provided that such shape, profile, or geometry does not deleteriously affect the reservoir (such as, for example, by puncturing the reservoir material if a pointed profile is too sharp). Also, the protrusion could extend into the cassette any desired distance—for example, about one-quarter or about one-third of the overall width of the cassette—and be located on any suitable surface of the cassette. In general, a protrusion as described by example or otherwise contemplated herein could have any desired shape, profile, geometry, size, and location, provided that the protrusion functions to satisfactorily create and maintain a desired crease or fold as aforedescribed.

Figure 5:
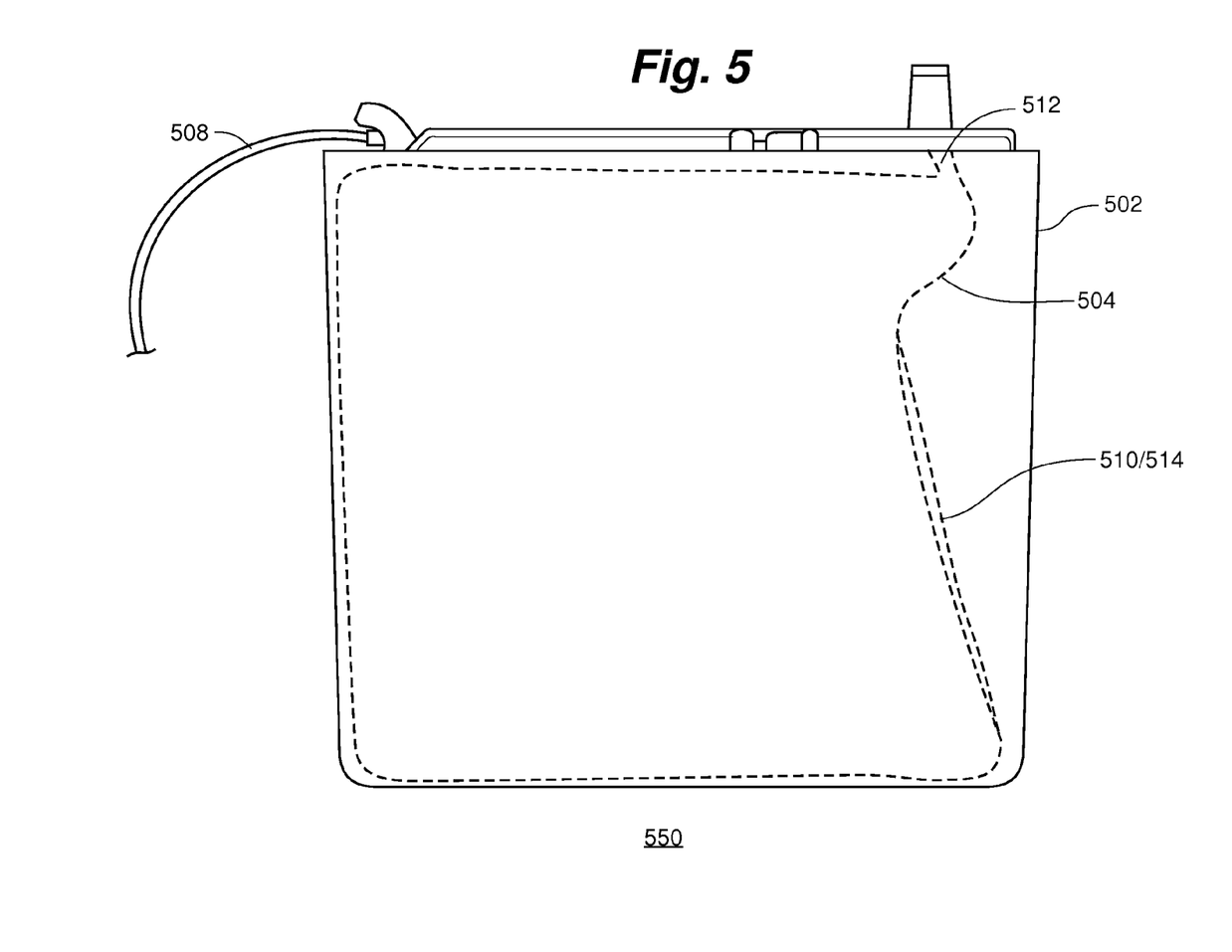
FIG. 5 is a front illustration of another embodiment of a cassette and reservoir assembly according to subject matter hereof.

In addition to or alternatively to the example of a protrusion shown in FIG. 4, film material used to create the flexible reservoir could be sealed along at least a portion thereof, within edges of the reservoir, to similarly create a channel for directing fluid flow to the outlet port. Thus, in another example embodiment, and referring now to FIG. 5, cassette and reservoir assembly 550 includes a cassette 502 and a reservoir 504 enclosed within cassette 502. At least one seal 514 could be provided in reservoir 504, by way of, for example, sealing together the material of the flexible reservoir along a selected portion thereof as shown by example in the drawing. Seal 514 is configured to create and maintain a crease or fold 510 along a surface of reservoir 504 as it empties, thereby creating a defined path or channel for a fluid within reservoir 504 to eventually flow to outlet port 512 and then outwardly to tube 508 in use and operation of assembly 550. Seal 514 could be formed by means of heat sealing, ultrasonic welding or sealing, or any of a variety of methodologies used for sealing polymeric films. In some embodiments this sealing technique could be provided only at an outermost edge or outermost edges, so that a total volume capacity of the reservoir would not otherwise be undesirably decreased. The channel so formed could extend along at least a portion of the length or width of the reservoir, with an end of the channel terminating proximate to or adjacent the outlet port. In a particular non-limiting embodiment, more than one channel is formed, thereby defining a grid or other pattern for channeling and facilitating flow of the fluid through and out of the outlet port.

Figure 6:
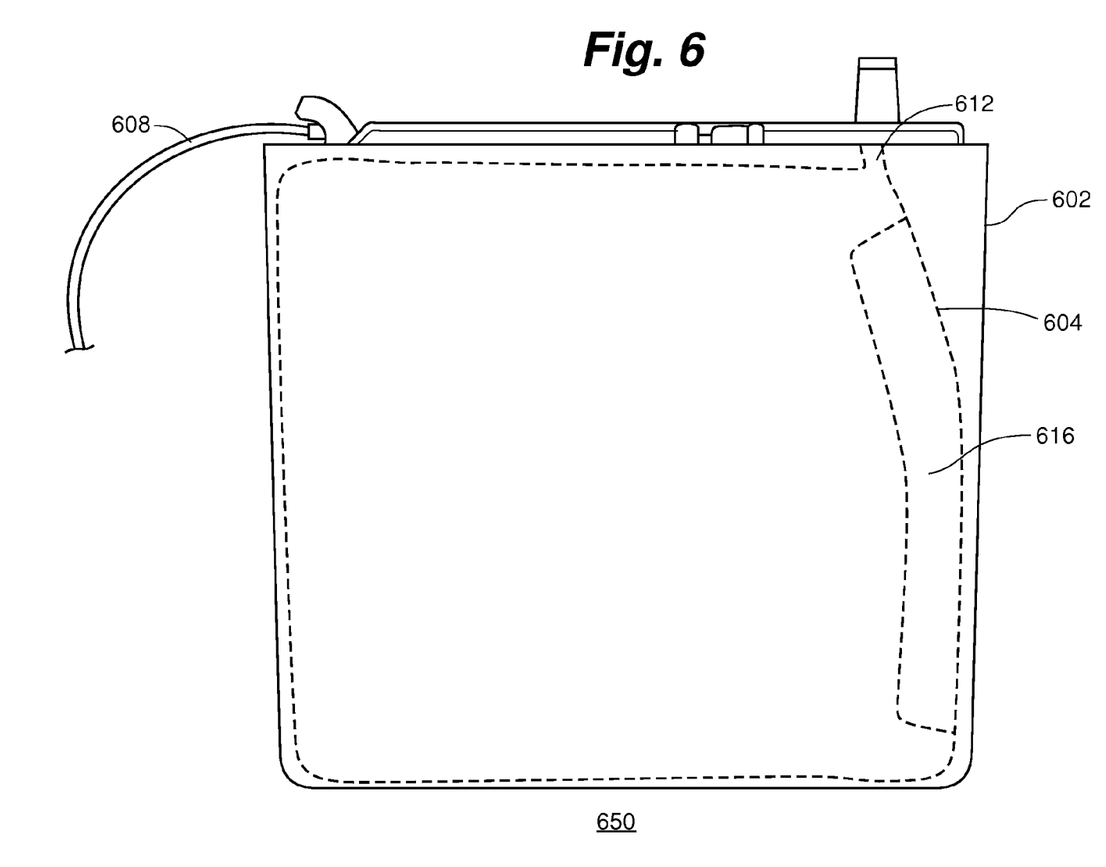
FIG. 6 is a front illustration of another embodiment of a cassette and reservoir assembly according to subject matter hereof.

In another example embodiment, in addition to or alternatively to any or all of the previously described example embodiments, a material flap could be formed within the reservoir. Thus, in one embodiment, and referring now to FIG. 6, cassette and reservoir assembly 650 includes a cassette 602 and a reservoir 604 enclosed within cassette 602. At least one flap 616 could be provided in reservoir 604, by way of, for example, an extension of a wall of the reservoir itself, or by way of a separate piece of polymer film or other material placed within and secured to the reservoir during manufacture. Similarly to the examples of various embodiments above, flap 616 could create a fluid path or channel extending along at least a portion of the length or width of reservoir 604, with, in some embodiments, an end of flap 616 terminating proximate to or adjacent to outlet port 612 for facilitating flow of fluid to outlet port 612 and then outwardly to tube 608 in use and operation of assembly 650.

Figure 7:
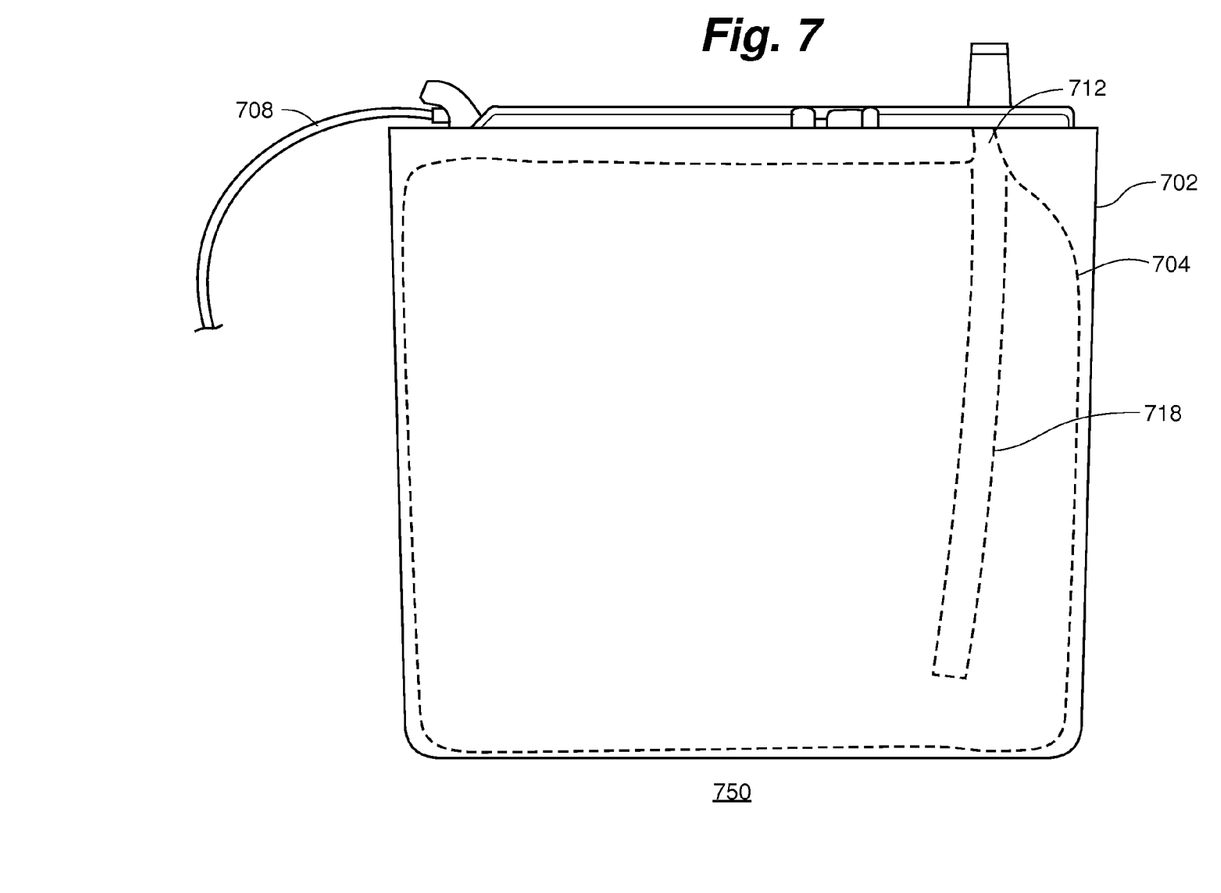
FIG. 7 is a front illustration of another embodiment of a cassette and reservoir assembly according to subject matter hereof.

In another example embodiment, in addition to or alternatively to any or all of the previously described example embodiments, and referring to FIG. 7, a cassette and reservoir assembly 750 includes a cassette 702 and a reservoir 704, and a tube 718 in fluid communication with reservoir 704. A portion of tube 718 extends within reservoir 704 from outlet port 712, and along at least a portion of a height or width of reservoir 704. As reservoir 704 empties under vacuum via a pumping mechanism, fluid in reservoir 704 flows along and/or within tube 718, thereby facilitating relatively consistent fluid flow from reservoir 704. As reservoir 704 empties, it collapses around tube 718, to reduce the likelihood of reservoir 704 sealing off pockets of fluid. Instead, by way of tube 718, a single channel or fluid path tends to be maintained until reservoir 704 is satisfactorily emptied.

Although not specifically illustrated, in another embodiment the tube itself (for example, tube 708 in FIG. 7) that is in fluid communication with the reservoir in the cassette and reservoir assembly, could be provided in a length that is greater than a typical length. Usually the tube protrudes or extends into the reservoir a small length—being just sufficient for the outlet port to be able to create a sufficient seal around the tube. But in such an embodiment, flexible reservoir material would advantageously tend to collapse and crease around the tube as the reservoir is emptied, thus reducing the likelihood of the reservoir sealing off pockets of fluid as aforedescribed.

Figure 8:
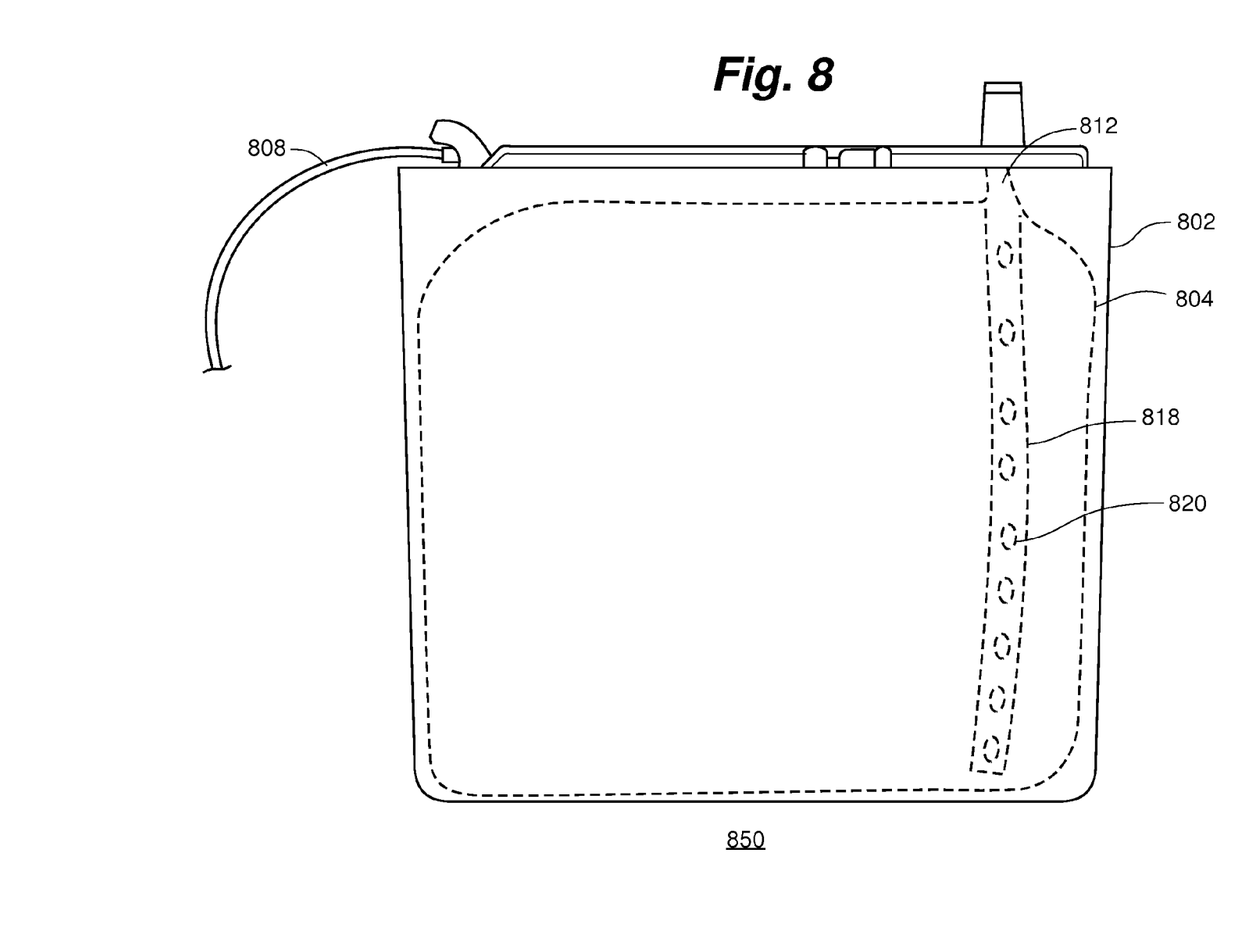
FIG. 8 is a front illustration of another embodiment of a cassette and reservoir assembly according to subject matter hereof.

In another example embodiment, in addition to or alternatively to any or all of the previously described example embodiments, and referring to FIG. 8, a cassette and reservoir assembly 850 includes a tube 818, similar to the example of tube 718 in FIG. 7. Tube 818 further includes a plurality of apertures 820 along a least a portion of a length of tube 818. Apertures 820 facilitate fluid flow not only along an exterior of tube 818, but also within tube 818. In this example, and as aforedescribed, tube 818 could be either a continuous extension of tube 808 that is connected to outlet port 812, or a separate tube sealed within reservoir 804.

It is to be appreciated and understood that, although not illustrated, a tube within a reservoir such as described by example above or otherwise contemplated herein, for promotion of channeling fluid toward an outlet port as the reservoir empties, could be provided as "freely floating" within the reservoir. In such an embodiment, the tube would not necessarily be connected to the outlet port and could, in some embodiments, essentially act as a protrusion in the cassette and reservoir assembly as aforedescribed to create and maintain a crease or fold along a surface of the reservoir as it empties.

Figure 9:
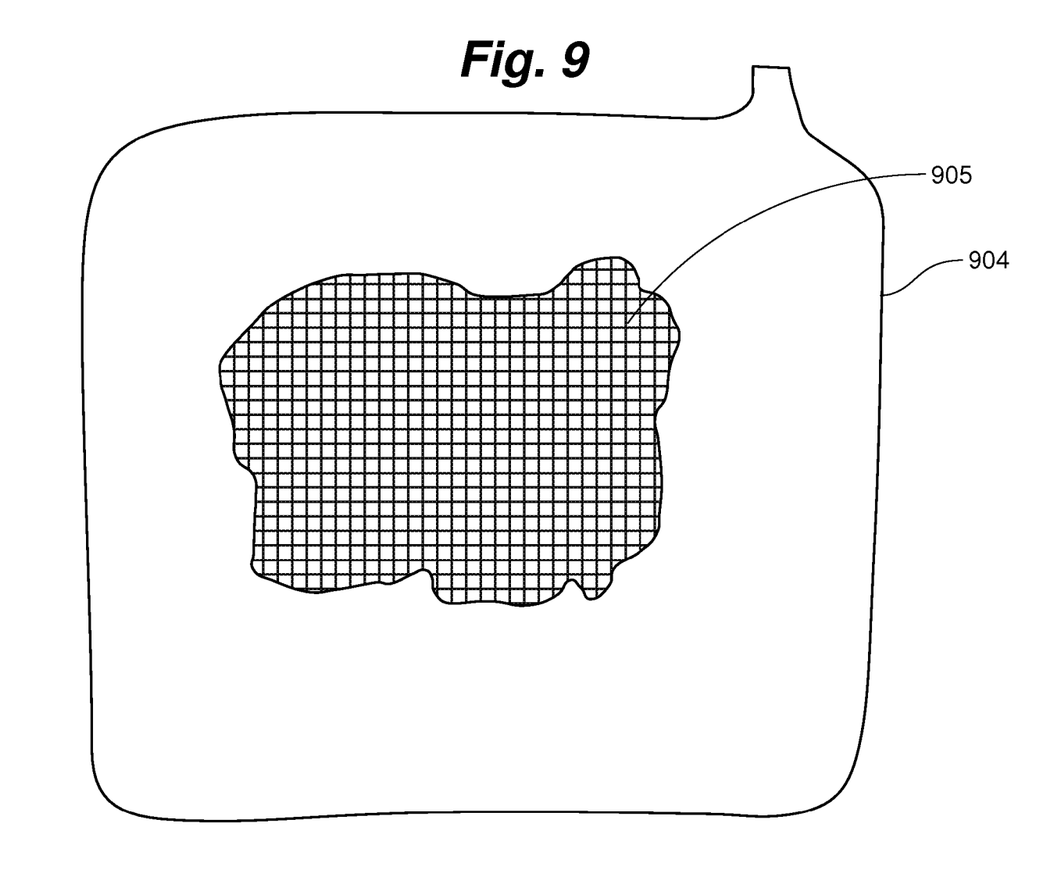
FIG. 9 is a front illustration of a reservoir according to another embodiment of subject matter hereof.
Figure 10:
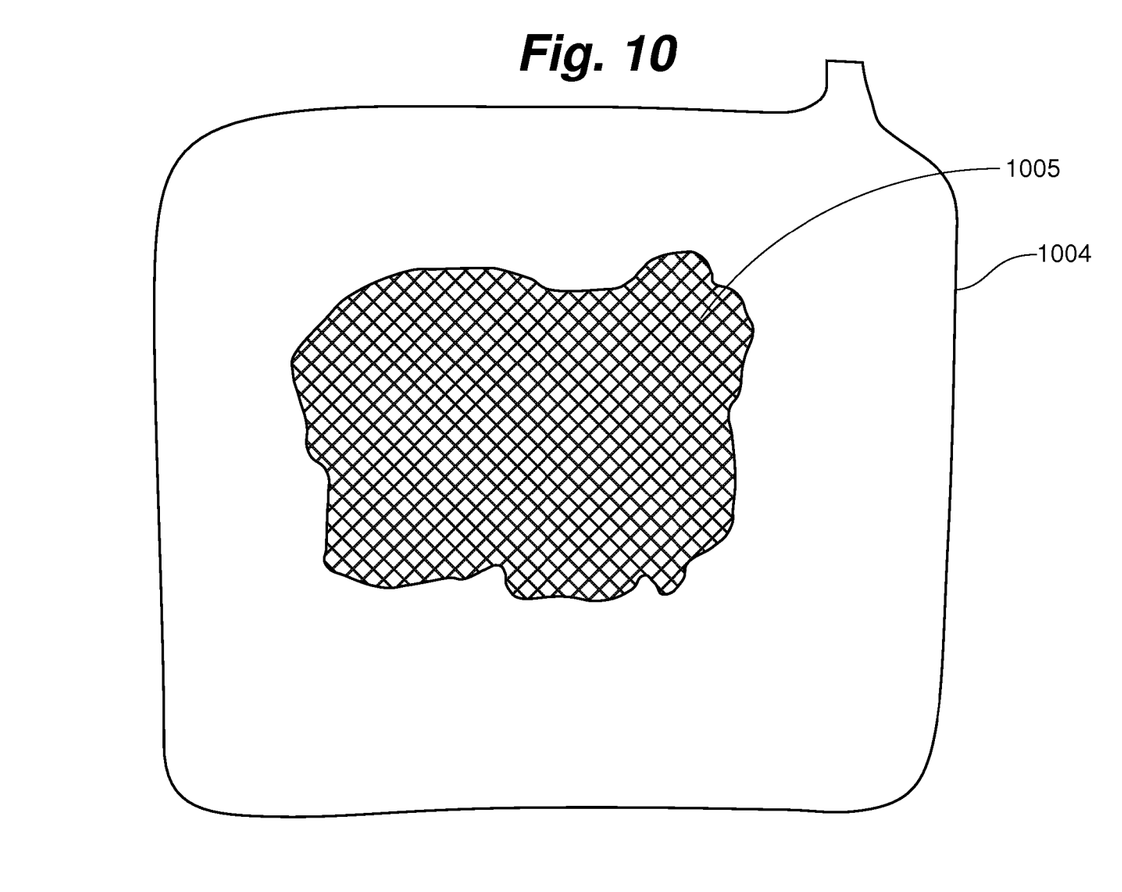
FIG. 10 is a front illustration of a reservoir according to another embodiment of subject matter hereof.

In another example embodiment, in addition to or alternatively to any or all of the previously described example embodiments, and referring now to FIG. 9, a reservoir 904 includes a textured interior surface 905 defining a plurality of raised surfaces and channels therein between for facilitating fluid flow within the reservoir to an outlet port. A cassette that typically would enclose the reservoir has been omitted from the drawing for simplicity. Although depicted in FIG. 9 as generally defining square profiles, it is to be appreciated that surface 905 in a particular embodiment could comprise any of a variety of polygonal or rounded three-dimensional shapes and profiles including, but not limited to, triangles, rectangles, circles, or combinations thereof, whether regular or irregular. Thus, in another example embodiment as shown in FIG. 10, a textured interior surface 1005 of a reservoir 1004 defines a plurality of raised surfaces and channels having generally "taffeta," "quilted," or diamond-shaped profiles.

It is to be appreciated and understood that, irrespective of a particular embodiment, in most instances provision of a "surface discontinuity" in the reservoir promotes fluid flow outwardly from the reservoir and more complete and consistent emptying thereof. In this regard, a surface discontinuity could be provided by virtually any suitably functioning structure in the cassette, the reservoir, or both. For example, the aforementioned cassette protrusions, film material seals, and reservoir tubes and textures could each provide such an advantageous surface discontinuity and assist in prevention of sealing off pockets of fluid in the reservoir and in channeling and flowing of the fluid outwardly from the reservoir.

In a typical reservoir, a combined outlet and filling port is located in one of the top corners such that it is proximate to the outlet port of the cassette within which the reservoir is contained. Typically, the combined outlet and filling port functions to both initially fill the reservoir before use and drain the reservoir during use. However, and although not illustrated, in another embodiment, in addition to or alternatively to any or all of the previously described example embodiments, the outlet or filling port is located elsewhere on the reservoir to facilitate fluid flow therethrough and out therefrom. For example, the outlet or filling port can be positioned towards the bottom of the reservoir for utilization of gravitational forces to aid in satisfactory reservoir emptying as aforedescribed. In such an embodiment, the outlet port of the cassette could be formed in a bottom, or toward a bottom, of the cassette; or the tubing could extend from the outlet or filling port of the reservoir within the cassette and out of an aperture in the top plate of the cassette. Furthermore, although not illustrated, in another embodiment an additional, second port could be provided. The presence of a second port would essentially tend to advantageously act as a surface discontinuity to promote channeling and flow of fluid from the reservoir as aforedescribed. Provision of a second port could also enable an easier reservoir filling process by way of fluid introduction through the second port, rather than through a female connector on output tubing associated with the outlet port as is commonly utilized with known cassette and reservoir assemblies. A second port could also facilitate more complete filling of the reservoir, by aiding in air removal from the reservoir through the outlet port as the reservoir is filled via the separate second port.

As discussed throughout this document, it is to be appreciated and understood that any one embodiment could be combined with any one or more of the other embodiments described by example or otherwise contemplated herein. For example, in one embodiment, a perforated tube could extend within the reservoir; and a protrusion on the interior surface of the cassette could facilitate folding or creasing of that reservoir along or around the perforated tube.

As known to those of skill in the art, an infusion pump typically operates in so-called peristaltic fashion wherein its pump mechanism essentially squeezes and releases fluid tubing to achieve pumping of fluid from the cassette reservoir to the patient. Such actions typically employ, e.g., cam/follower, finger type, and roller type components that move in cooperation with, e.g., valves, expulsers, or other similar components in the pump. Thus, in operation of fluid delivery device 20, a patient could, for example, request delivery of therapeutic fluid such as pain medication by requesting what otherwise could be deemed a bolus of a fluid medication through control module 202. In this regard, such a request could be delivered by the patient through a medication dose request device (not illustrated) that could in turn be, e.g., the aforementioned remote dose cord device or voice-activated or speech recognition device. In one embodiment, the medication dose request device could be in wired communication with control module 202 by way of, for example, connection to remote dosing command port 218 as shown in FIG. 2. Alternatively, although not illustrated, such communication between the medication dose request device and the control module could be provided by a suitable wireless or other desired connection.

While drug or fluid delivery devices have been particularly shown and described with reference to the accompanying figures and specification, it should be understood however that other modifications thereto are of course possible; and all of them are intended to be within the true spirit and scope of novel and inventive drug or fluid delivery devices described herein.

It should also be appreciated that types, components, dimensions, fabrication processes, and other particulars and parameters of afore described example embodiments may be substituted for others as desired, or that accessories may be added thereto. Further, drug or fluid delivery devices described by example or otherwise contemplated herein might be capable of including any of the following features or functions, separately or in various combinations, such as for example: (i) providing an electronically stored drug library in the control module for the drug or fluid contained within the reservoir, for enforcing administration limits; (ii) providing a means for dispensing multiple doses of medication or fluid in response to a single dispensing command, when so prescribed; (iii) adapting the cassette to (a) use "off-the-shelf" pharmacy unit dose packaging equipment, (b) be for a single use and disposable, or for multiple uses and refillable, and (c) be locked shut when it is latched or otherwise locked onto the pump; and (iv) providing a means—whether electronically, visually, or both—for determining or logging how much medication or fluid is in a cassette and when the medication or fluid is approaching empty.

It is also to be understood in general that any suitable alternatives may be employed to provide novel and inventive drug or fluid delivery devices described herein.

Lastly, compositions, sizes, and strengths of various aforementioned components of novel and inventive drug or fluid delivery devices described herein are all a matter of design choice depending upon intended uses thereof.

Accordingly, these and other various changes or modifications in form and detail may also be made, without departing from the true spirit and scope of novel and inventive drug or fluid delivery devices defined by the appended claims.

It should also be appreciated that the exemplary embodiment or exemplary embodiments are only examples, and are not intended to limit the scope, applicability, or configuration of the subject matter hereof in any way. Rather, the foregoing detailed description will provide those skilled in the art with an enabling disclosure for implementing the exemplary embodiment or exemplary embodiments. It should be understood that various changes can be made in the function and arrangement of elements without departing from the scope of the subject matter hereof as set forth in the appended claims and the legal equivalents thereof.

The embodiments above are intended to be illustrative and not limiting. Additional embodiments are within the claims. Although the present subject matter has been described with reference to particular embodiments, workers skilled in the art will recognize that changes may be made in form and detail without departing from the spirit and scope of the subject matter hereof.

Various modifications to the subject matter hereof may be apparent to one of skill in the art upon reading this disclosure. For example, persons of ordinary skill in the relevant art will recognize that the various features described for the different embodiments of the subject matter can be suitably combined, un-combined, and re-combined with other features, alone, or in different combinations, within the spirit of the subject matter hereof. Accordingly, the embodiments are not mutually exclusive combinations of features; rather, the invention can comprise a combination of different individual features selected from different individual embodiments, as understood by persons of ordinary skill in the art. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended. Furthermore, it is intended also to include features of a claim in any other independent claim even if this claim is not directly made dependent to the independent claim. Likewise, the various features described above should all be regarded as example embodiments, rather than limitations to the scope or spirit of the subject matter hereof. Therefore, the above is not contemplated to limit the scope of the present subject matter hereof.

Any incorporation by reference of documents above is limited such that no subject matter is incorporated that is contrary to the explicit disclosure herein. Any incorporation by reference of documents above is further limited such that any definitions provided in the documents are not incorporated by reference herein unless expressly included herein.

For purposes of interpreting the claims for the present subject matter, it is expressly intended that the provisions of Section 112, sixth paragraph of 35 U.S.C. are not to be invoked unless the specific terms "means for" or "step for" are recited in a claim.

What is claimed is:

1. A drug or fluid delivery device, comprising:
   a pump having a control module;
   a cassette that is removably mounted to said control module;
   a reservoir contained within said cassette, said reservoir containing a fluid to be delivered to a patient; and
   a protrusion extending from an interior surface of said cassette, said protrusion creating and maintaining a crease in said reservoir as the fluid is emptied from said reservoir in operation of said device, thereby creating a fluid path along which the fluid travels to reduce occurrences of said reservoir deleteriously sealing off pockets of fluid as said reservoir is emptied.

* * * * *